US007777067B2

(12) United States Patent
Fukuoka et al.

(10) Patent No.: US 7,777,067 B2
(45) Date of Patent: Aug. 17, 2010

(54) INDUSTRIAL PROCESS FOR PRODUCTION OF AN AROMATIC CARBONATE

(75) Inventors: Shinsuke Fukuoka, Tokyo (JP); Hiroshi Hachiya, Tokyo (JP); Kazuhiko Matsuzaki, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 666 days.

(21) Appl. No.: 11/632,214

(22) PCT Filed: Jul. 11, 2005

(86) PCT No.: PCT/JP2005/012778

§ 371 (c)(1),
(2), (4) Date: Jan. 11, 2007

(87) PCT Pub. No.: WO2006/006566

PCT Pub. Date: Jan. 19, 2006

(65) Prior Publication Data
US 2007/0265461 A1 Nov. 15, 2007

(30) Foreign Application Priority Data
Jul. 13, 2004 (JP) ............................. 2004-205602

(51) Int. Cl.
C07C 68/06 (2006.01)
C07C 68/08 (2006.01)
(52) U.S. Cl. .................... 558/274; 558/260; 558/270
(58) Field of Classification Search ................ 558/260, 558/270, 274
See application file for complete search history.

(56) References Cited

U.S. PATENT DOCUMENTS

| 4,045,464 | A | 8/1977 | Romano et al. |
| 4,182,726 | A | 1/1980 | Illuminati et al. |
| 4,252,737 | A | 2/1981 | Krimm et al. |
| 4,410,464 | A | 10/1983 | Hallgren |
| 4,552,704 | A | 11/1985 | Mark |
| 4,554,110 | A | 11/1985 | Mark |
| 4,609,501 | A | 9/1986 | Mark |
| 5,210,268 | A | 5/1993 | Fukuoka et al. |
| 5,231,212 | A | 7/1993 | Buysch et al. |
| 5,282,965 | A | 2/1994 | Urairi et al. |
| 5,284,965 | A | 2/1994 | Buysch et al. |
| 5,334,742 | A | 8/1994 | Schon et al. |
| 5,344,954 | A | 9/1994 | Schon et al. |
| 5,359,118 | A | 10/1994 | Wagner et al. |
| 5,362,901 | A | 11/1994 | Wagner et al. |
| 5,426,207 | A | 6/1995 | Harrison et al. |
| 5,495,038 | A | 2/1996 | Buysch et al. |
| 5,705,673 | A | 1/1998 | Rivetti et al. |
| 5,747,609 | A | 5/1998 | Komiya et al. |
| 5,872,275 | A | 2/1999 | Komiya et al. |
| 6,093,842 | A | 7/2000 | Oyevaar et al. |
| 6,197,916 | B1 | 3/2001 | Pressman et al. |
| 6,262,210 | B1 | 7/2001 | Tojo et al. |
| 6,346,638 | B1 | 2/2002 | Tojo et al. |
| 6,479,689 | B1 | 11/2002 | Tojo et al. |
| 6,861,494 | B2 | 3/2005 | Debruin |
| 7,417,161 | B2 | 8/2008 | Woo et al. |
| 7,622,601 | B2 | 11/2009 | Fukuoka et al. |
| 2001/0021786 | A1 | 9/2001 | Bruin et al. |
| 2002/0107355 | A1 | 8/2002 | Bouwens et al. |
| 2004/0236136 | A1 | 11/2004 | Schlosberg et al. |
| 2004/0266974 | A1 | 12/2004 | Murthy et al. |

(Continued)

FOREIGN PATENT DOCUMENTS

DE 736063 6/1943

(Continued)

OTHER PUBLICATIONS

US Office Action for co-pending U.S. Appl. No. 11/660,362 issued Dec. 17, 2009.

*Primary Examiner*—Kamal A Saeed
*Assistant Examiner*—Samantha L Shterengarts
(74) *Attorney, Agent, or Firm*—Birch, Stewart, Kolasch & Birch, LLP

(57) ABSTRACT

It is an object of the present invention to provide, for the case of continuously producing aromatic carbonates containing a diaryl carbonate as a main product by taking an alkyl aryl carbonate as a starting material, which is obtainable through a transesterification reaction between a dialkyl carbonate and an aromatic monohydroxy compound, using a continuous multi-stage distillation column in which a catalyst is present, and continuously feeding the starting material into the continuous multi-stage distillation column, a specific process that enables the diaryl carbonate to be produced with high selectivity and high productivity stably for a prolonged period of time on an industrial scale of not less than 1 ton per hour. Although there have been various proposals regarding processes for the production of aromatic carbonates by means of a reactive distillation method, these have all been on a small scale and short operating time laboratory level, and there have been no disclosures whatsoever on a specific process or apparatus enabling mass production on an industrial scale. According to the present invention, there is provided a specified continuous multi-stage distillation column, and there is also provided a specific process that enables a diaryl carbonate to be produced with high selectivity and high productivity stably for a prolonged period of time on an industrial scale of not less than 1 ton per hour from an alkyl aryl carbonate.

17 Claims, 1 Drawing Sheet

U.S. PATENT DOCUMENTS

| | | |
|---|---|---|
| 2007/0191623 A1 | 8/2007 | Fukuoka et al. |
| 2007/0219387 A1 | 9/2007 | Fukuoka et al. |
| 2007/0255069 A1 | 11/2007 | Fukuoka et al. |
| 2007/0260083 A1 | 11/2007 | Fukuoka et al. |
| 2007/0260084 A1 | 11/2007 | Fukuoka et al. |
| 2007/0260095 A1 | 11/2007 | Fukuoka et al. |
| 2007/0270604 A1 | 11/2007 | Fukuoka et al. |
| 2008/0041712 A1 | 2/2008 | Fukuoka et al. |
| 2008/0051595 A1 | 2/2008 | Fukuoka et al. |
| 2008/0064846 A1 | 3/2008 | Fukuoka et al. |
| 2008/0221348 A1 | 9/2008 | Fukuoka et al. |
| 2008/0223711 A1 | 9/2008 | Fukuoka et al. |
| 2009/0118530 A1 | 5/2009 | Fukuoka et al. |

FOREIGN PATENT DOCUMENTS

| | | |
|---|---|---|
| EA | 009715 B1 | 2/2008 |
| EA | 010066 B1 | 6/2008 |
| EP | 0 461 274 A1 | 12/1991 |
| EP | 0530615 A2 | 3/1993 |
| EP | 0560159 A1 | 9/1993 |
| EP | 0569812 A1 | 11/1993 |
| EP | 0582930 A2 | 2/1994 |
| EP | 0582931 A2 | 2/1994 |
| EP | 0722931 A1 | 7/1996 |
| EP | 0 784 048 A1 | 7/1997 |
| EP | 0781760 A1 | 7/1997 |
| EP | 0855384 A1 | 7/1998 |
| EP | 0892001 A1 | 1/1999 |
| EP | 1016648 A1 | 7/2000 |
| EP | 1086940 A1 | 3/2001 |
| EP | 1174406 A1 | 1/2002 |
| EP | 1 762 559 A1 | 3/2007 |
| EP | 1 762 560 A1 | 3/2007 |
| EP | 1760069 A1 | 3/2007 |
| EP | 1767518 A1 | 3/2007 |
| EP | 1 783 112 A1 | 5/2007 |
| EP | 1 787 977 A1 | 5/2007 |
| EP | 1792890 A1 | 6/2007 |
| EP | 1795523 A1 | 6/2007 |
| IT | 1255746 B | 11/1995 |
| JP | 51-75044 B | 6/1976 |
| JP | 51-105032 A | 9/1976 |
| JP | 54-48732 A | 4/1979 |
| JP | 54-48733 A | 4/1979 |
| JP | 54-63023 A | 5/1979 |
| JP | 56-25138 | 3/1981 |
| JP | 56-123948 A | 9/1981 |
| JP | 56-123949 A | 9/1981 |
| JP | 57-176932 A | 10/1982 |
| JP | 57-183745 A | 11/1982 |
| JP | 58-185536 A | 10/1983 |
| JP | 60-169444 A | 9/1985 |
| JP | 60-169445 A | 9/1985 |
| JP | 60-173016 A | 9/1985 |
| JP | 61-172852 A | 8/1986 |
| JP | 61-291545 A | 12/1986 |
| JP | 62-277345 A | 12/1987 |
| JP | 1-93560 A | 4/1989 |
| JP | 1-265062 A | 10/1989 |
| JP | 1-265063 A | 10/1989 |
| JP | 1-265064 A | 10/1989 |
| JP | 3-291257 A | 12/1991 |
| JP | 4-9358 A | 1/1992 |
| JP | 4-100824 A | 4/1992 |
| JP | 4-198141 A | 7/1992 |
| JP | 4-211038 A | 8/1992 |
| JP | 4-224547 A | 8/1992 |
| JP | 4-230242 A | 8/1992 |
| JP | 4-235951 A | 8/1992 |
| JP | 5-213830 A | 8/1993 |
| JP | 6-9506 A | 1/1994 |
| JP | 6-9507 A | 1/1994 |
| JP | 6-41022 A | 2/1994 |
| JP | 6-157424 A | 6/1994 |
| JP | 6-184058 A | 7/1994 |
| JP | 7-101908 A | 4/1995 |
| JP | 7-304713 A | 11/1995 |
| JP | 9-40616 A | 2/1997 |
| JP | 9-59224 A | 3/1997 |
| JP | 9-59225 A | 3/1997 |
| JP | 9-110805 A | 4/1997 |
| JP | 9-165357 A | 6/1997 |
| JP | 9-169704 A | 6/1997 |
| JP | 9-173819 A | 7/1997 |
| JP | 9-176094 A | 7/1997 |
| JP | 9-194435 A | 7/1997 |
| JP | 9-194436 A | 7/1997 |
| JP | 9-194437 A | 7/1997 |
| JP | 9-255772 A | 9/1997 |
| JP | 10-245366 A | 9/1998 |
| JP | 11-12230 A | 1/1999 |
| JP | 11-49727 A | 2/1999 |
| JP | 11-92429 A | 4/1999 |
| JP | 11-228504 A | 8/1999 |
| JP | 2000-191596 A | 7/2000 |
| JP | 2000-191597 A | 7/2000 |
| JP | 2001-64234 A | 3/2001 |
| JP | 2001-64235 A | 3/2001 |
| JP | 2003-113144 A | 4/2003 |
| JP | 2003-119168 A | 4/2003 |
| JP | 2003-155264 A | 5/2003 |
| JP | 2003-516376 A | 5/2003 |
| JP | 2003-300936 A | 10/2003 |
| JP | 2003-342209 A | 12/2003 |
| JP | 2004-131421 A | 4/2004 |
| JP | 2004-323384 A | 11/2004 |
| JP | 2006-182683 A | 7/2006 |
| JP | 2006-199643 A | 8/2006 |
| JP | 2006-206497 A | 8/2006 |
| RU | 2041869 C1 | 8/1995 |
| WO | WO-91/09832 A1 | 7/1991 |
| WO | WO92/18458 A1 | 10/1992 |
| WO | WO-97/11049 A1 | 3/1997 |
| WO | WO-99/64382 A1 | 12/1999 |
| WO | WO-99/64492 A1 | 12/1999 |
| WO | WO-00/18720 A1 | 4/2000 |
| WO | WO-00/51954 A1 | 9/2000 |
| WO | WO-01/42187 A1 | 6/2001 |
| WO | WO-02/40439 A2 | 5/2002 |
| WO | WO-03/016257 A1 | 2/2003 |
| WO | WO-03/066569 A1 | 8/2003 |
| WO | WO-2005/123638 A1 | 12/2005 |
| WO | WO-2006/001256 A1 | 1/2006 |
| WO | WO-2006/022294 A1 | 3/2006 |
| WO | WO-2006/025424 A1 | 3/2006 |
| WO | WO-2006-025478 A | 3/2006 |
| WO | WO-2006/041075 A1 | 4/2006 |

INDUSTRIAL PROCESS FOR PRODUCTION OF AN AROMATIC CARBONATE

TECHNICAL FIELD

The present invention relates to an industrial process for the production of an aromatic carbonate. More particularly, the present invention relates to an industrial process for the production of a large amount of an aromatic carbonate useful as a raw material of a transesterification method polycarbonate by taking an alkyl aryl carbonate as a starting material, which is obtainable through a transesterification reaction between a dialkyl carbonate and an aromatic monohydroxy compound, and by converting this starting material into aromatic carbonates containing a diaryl carbonate as a main product therein in a continuous multi-stage distillation column in which a catalyst is present.

BACKGROUND ART

An aromatic carbonates is important as a raw material for the production of aromatic polycarbonate which is the most widely used engineering plastic, without using toxic phosgene. As a process for producing an aromatic carbonate, a process of reacting an aromatic monohydroxy compound with phosgene has been known from long ago, and has also been the subject of a variety of studies in recent years. However, this process has the problem of using phosgene, and in addition chlorinated impurities that are difficult to separate out are present in the aromatic carbonate produced using this process, and hence the aromatic carbonate cannot be used as the raw material for the production of the aromatic polycarbonate. Because such chlorinated impurities markedly inhibit the polymerization reaction in the transesterification method which is carried out in the presence of an extremely small amount of a basic catalyst; for example, even if such chlorinated impurities are present in an amount of only 1 ppm, the polymerization hardly proceeds at all. To make the aromatic carbonate capable of being used as the raw material of polycarbonate of the transesterification method, troublesome multi-stage separation/purification processes such as enough washing with a dilute aqueous alkaline solution and hot water, oil/water separation, distillation and so on are thus required. Furthermore, the yield of the aromatic carbonate decreases due to hydrolysis loss during this separation/purification processes. Therefore, there are many problems in carrying out this method economically on an industrial scale.

On the other hand, a process for producing aromatic carbonates through transesterification reactions between a dialkyl carbonate and an aromatic monohydroxy compound is also known. However, such transesterification reactions are all equilibrium reactions. Since the equilibriums are biased extremely toward the original system and the reaction rates are slow, and hence there have been many difficulties in producing aromatic carbonates industrially in large amounts using this method. Several proposals have been made to improve on the above difficulties, but most of these have related to development of a catalyst to increase the reaction rate. Many metal compounds have been proposed as catalysts for this type of transesterification reaction. For example, Lewis acids such as a transition metal halide and Lewis acid-forming compounds (see Patent Documents 1: Japanese Patent Application Laid-Open No. 51-105032, Japanese Patent Application Laid-Open No. 56-123948, Japanese Patent Application Laid-Open No. 56-123949 (corresponding to West German Patent Application No. 2528412, British Patent No. 1499530, and U.S. Pat. No. 4,182,726), Japanese Patent Application Laid-Open No. 51-75044 (corresponding to West German Patent Application No. 2552907, and U.S. Pat. No. 4,045,464)), tin compounds such as an organo-tin alkoxide and an organo-tin oxides (see Patent Documents 2: Japanese Patent Application Laid-Open No. 54-48733 (corresponding to West German Patent Application No. 2736062), Japanese Patent Application Laid-Open No. 54-63023, Japanese Patent Application Laid-Open No. 60-169444 (corresponding to U.S. Pat. No. 4,554,110), Japanese Patent Application Laid-Open No. 60-169445 (corresponding to U.S. Pat. No. 4,552,704), Japanese Patent Application Laid-Open No. 62-277345, Japanese Patent Application Laid-Open No. 1-265063, Japanese Patent Application Laid-Open No. 60-169444 (corresponding to U.S. Pat. No. 4,554,110), Japanese Patent Application Laid-Open No. 60-169445 (corresponding to U.S. Pat. No. 4,552,704), Japanese Patent Application Laid-Open No. 62-277345, Japanese Patent Application Laid-Open No. 1-265063), salts and alkoxides of alkali metals and alkaline earth metals (see Patent Document 3: Japanese Patent Application Laid-Open No. 57-176932), lead compounds (see Patent Documents 4: Japanese Patent Application Laid-Open No. 57-176932, Japanese Patent Application Laid-Open No. 1-93560), complexes of metals such as copper, iron and zirconium (see Patent Document 5: Japanese Patent Application Laid-Open No. 57-183745), titanic acid esters (see Patent Documents 6: Japanese Patent Application Laid-Open No. 58-185536 (corresponding to U.S. Pat. No. 4,410,464), Japanese Patent Application Laid-Open No. 1-265062), mixtures of a Lewis acid and a protonic acid (see Patent Document 7: Japanese Patent Application Laid-Open No. 60-173016 (corresponding to U.S. Pat. No. 4,609,501)), compounds of Sc, Mo, Mn, Bi, Te or the like (see Patent Document 8: Japanese Patent Application Laid-Open No. 1-265064), ferric acetate (see Patent Document 9: Japanese Patent Application Laid-Open No. 61-172852), and so on have been proposed. However, the problem of the disadvantageous equilibrium cannot be solved merely by developing the catalyst, and hence there are very many issues to be solved including the reaction system in order to provide a process for the industrial production aiming for mass production.

Attempts have also been made to devise a reaction system so as to shift the equilibrium toward the product system as much as possible, and thus improve the yield of the aromatic carbonates. For example, for the reaction between dimethyl carbonate and phenol, there have been proposed a method in which by-produced methanol is distilled off by azeotropy together with an azeotrope-forming agent (see Patent Document 10: Japanese Patent Application Laid-Open No. 54-48732 (corresponding to West German Patent Application No. 736063, and U.S. Pat. No. 4,252,737)), and a method in which the methanol produced as the by-product is removed by being adsorbed onto a molecular sieve (see Patent Document 11: Japanese Patent Application Laid-Open No. 58-185536 (corresponding to U.S. Pat. No. 410,464)). Moreover, a method has also been proposed in which, using an apparatus in which a distillation column is provided on top of a reactor, an alcohol produced as the by-product in the reaction is separated off from the reaction mixture, and at the same time unreacted starting material that evaporates is separated off by distillation (see Patent Documents 12: examples in Japanese Patent Application Laid-Open No. 56-123948 (corresponding to U.S. Pat. No. 4,182,726), examples in Japanese Patent Application Laid-Open No. 56-25138, examples in Japanese Patent Application Laid-Open No. 60-169444 (corresponding to U.S. Pat. No. 4,554,110), examples in Japanese Patent Application Laid-Open No. 60-169445 (corresponding to U.S. Pat. No. 4,552,704), examples in Japanese Patent Application Laid-Open No. 60-173016 (corresponding to U.S. Pat. No. 4,609,501), examples in Japanese Patent Application Laid-Open No. 61-172852, examples in Japanese Patent Application Laid-Open No. 61-291545, examples in Japanese Patent Application Laid-Open No. 62-277345).

However, these reaction systems are basically batch system or switchover system. Because there is the limitation in the improvement of the reaction rate through catalyst development for such a transesterification reaction, and the reaction rate is still slow, and thus it has been thought that a batch system is preferable to a continuous system. Of these, a continuous stirring tank reactor (CSTR) system in which a distillation column is provided on top of a reactor has been proposed as a continuous system, but there are problems such as the reaction rate being slow, and a gas-liquid interface in the reactor being small, based on the volume of the liquid. Hence it is not possible to make the conversion high. Accordingly, it is difficult to attain the object of producing the aromatic carbonate continuously in large amounts stably for a prolonged period of time by means of the above-mentioned methods, and many issues remain to be resolved before economical industrial implementation is possible.

The present inventors have developed reactive distillation methods in which such a transesterification reaction is carried out in a continuous multi-stage distillation column simultaneously with separation by distillation, and have been the first in the world to disclose that such a reactive distillation system is useful for such a transesterification reaction, for example a reactive distillation method in which a dialkyl carbonate and an aromatic hydroxy compound are continuously fed into a multi-stage distillation column, and the reaction is carried out continuously inside the column in which a catalyst is present, while continuously withdrawing a low boiling point component containing an alcohol produced as a by-product by distillation and continuously withdrawing a component containing a produced alkyl aryl carbonate from a lower portion of the column (see Patent Document 13: Japanese Patent Application Laid-Open No. 3-291257), a reactive distillation method in which an alkyl aryl carbonate is continuously fed into the multi-stage distillation column, and the reaction is carried out continuously inside the column in which a catalyst is present, while continuously withdrawing by distillation a low boiling point component containing a dialkyl carbonate produced as a by-product and continuously withdrawing a component containing a produced diaryl carbonate from a lower portion of the column (see Patent Document 14: Japanese Patent Application Laid-Open No. 4-9358), a reactive distillation method in which these reactions are carried out using two continuous multi-stage distillation columns, and hence a diaryl carbonate is produced continuously while efficiently recycling a dialkyl carbonate produced as a by-product (see Patent Document 15: Japanese Patent Application Laid-Open No. 4-211038), and a reactive distillation method in which a dialkyl carbonate and an aromatic hydroxy compound or the like are continuously fed into the multi-stage distillation column, and a liquid that flows down through the column is withdrawn from a side outlet provided at an intermediate stage and/or a lowermost stage of the distillation column, and is introduced into a reactor provided outside the distillation column so as to bring about reaction, and is then introduced back in through a circulating inlet provided at a stage above the stage where the outlet is provided, whereby reaction is carried out in both the reactor and the distillation column (see Patent Documents 16: Japanese Patent Application Laid-Open No. 4-224547, Japanese Patent Application Laid-Open No. 4-230242, Japanese Patent Application Laid-Open No. 4-235951).

These reactive distillation methods proposed by the present inventors are the first to enable aromatic carbonates to be produced continuously and efficiently, and many similar reactive distillation systems based on the above disclosures have been proposed thereafter (see Patent Documents 17 to 32: Patent Document 17: International Publication No. 00/18720 (corresponding to U.S. Pat. No. 5,362,901), Patent Document 18: Italian Patent No. 01255746, Patent Document 19: Japanese Patent Application Laid-Open No. 6-9506 (corresponding to European Patent No. 0560159, and U.S. Pat. No. 5,282,965), Patent Document 20: Japanese Patent Application Laid-Open No. 6-41022 (corresponding to European Patent No. 0572870, and U.S. Pat. No. 5,362,901), Patent Documents 21: Japanese Patent Application Laid-Open No. 6-157424 (corresponding to European Patent No. 0582931, and U.S. Pat. No. 5,334,742), Japanese Patent Application Laid-Open No. 6-184058 (corresponding to European Patent No. 0582930, and U.S. Pat. No. 5,344,954), Patent Document 22: Japanese Patent Application Laid-Open No. 7-304713, Patent Document 23: Japanese Patent Application Laid-Open No. 9-40616, Patent Document 24: Japanese Patent Application Laid-Open No. 9-59225, Patent Document 25: Japanese Patent Application Laid-Open No. 9-110805, Patent Document 26: Japanese Patent Application Laid-Open No. 9-165357, Patent Document 27: Japanese Patent Application Laid-Open No. 9-173819, Patent Documents 28: Japanese Patent Application Laid-Open No. 9-176094, Japanese Patent Application Laid-Open No. 2000-191596, Japanese Patent Application Laid-Open No. 2000-191597, Patent Document 29: Japanese Patent Application Laid-Open No. 9-194436 (corresponding to European Patent No. 0785184, and U.S. Pat. No. 5,705,673), Patent Document 30: International Publication No. 00/18720 (corresponding to U.S. Pat. No. 6,093, 842), Patent Documents 31: Japanese Patent Application Laid-Open No. 2001-64234, Japanese Patent Application Laid-Open No. 2001-64235, Patent Document 32: International Publication No. 02/40439 (corresponding to U.S. Pat. Nos. 6,596,894, 6,596,895, and 6,600,061)).

Among reactive distillation systems, the present applicants have further proposed, as a method that enables highly pure aromatic carbonates to be produced stably for a prolonged period of time without a large amount of a catalyst being required, a method in which high boiling point material containing a catalyst component is reacted with an active substance and then separated off, and the catalyst component is recycled (see Patent Documents 31: Japanese Patent Application Laid-Open No. 2001-64234, Japanese Patent Application Laid-Open No. 2001-64235), and a method carried out while keeping a weight ratio of a polyhydric aromatic hydroxy compound in the reaction system to a catalyst metal at not more than 2.0 (see Patent Document 32: International Publication No. 02/40439 (corresponding to U.S. Pat. Nos. 6,596,894, 6,596,895, and 6,600,061)). Furthermore, the present inventors have proposed a method in which 70 to 99% by weight of phenol produced as a by-product in a polymerization process is used as a starting material, and diphenyl carbonate can be produced by means of the reactive distillation method. This diphenyl carbonate can be used as the raw material for polymerization of aromatic polycarbonates (see Patent Document 33: International Publication No. 97/11049 (corresponding to European Patent No. 0855384, and U.S. Pat. No. 5,872,275)).

However, in all of these prior art documents in which the production of aromatic carbonates using the reactive distillation method is proposed, there is no disclosure whatsoever of a specific process or apparatus enabling mass production on an industrial scale (e.g. not less than 1 ton per hour), nor is there any description suggesting such a process or apparatus. For example, the descriptions regarding a height (H: cm), a diameter (D: cm), and the number of stages (n) of the reactive distillation column and a feeding rate of the raw material (Q: kg/hr) disclosed for producing diphenyl carbonate (DPC) from methyl phenyl carbonate (MPC) are as summarized in the following table.

TABLE 1

| H: cm | D: cm | NO. OF STAGE: n | Q: kg/hr | PATENT DOCUMENT |
|---|---|---|---|---|
| 400 | 7.5 | — | 4.2 | 14 |
| 600 | 25 | 20 | 23.3 | 15 |
| 305 | 5-10 | 15 + STRUCTURED PACKING | 0.6 | 21 |
| 400 | 8 | 50 | <0.6 | 23 |
| 200 | 4 | — | 0.8 | 24 |
| — | 5 | 25 | 0.7 | 28 |
| 600 | 25 | 20 | 31 | 33 |
| 600 | 25 | 20 | 31 | 34 |
| 600 | — | 20 | 22.3 | 35 |

See Patent Document 34: Japanese Patent Application Laid-Open No. 11-92429 (corresponding to European Patent No. 1016648, and U.S. Pat. No. 6,262,210 See Patent document 35: Japanese Patent Application Laid-Open No. 9-255772 (corresponding to European Patent No. 0892001, and U.S. Pat. No. 5,747,609)

In other words, the biggest continuous multi-stage distillation columns used when carrying out this reaction using the reactive distillation system are those disclosed by the present applicants in Patent Documents 15, 33 and 34. As can be seen from Table 1, the maximum values of the various conditions for the continuous multi-stage distillation columns disclosed for the above reaction are H=600 cm, D=25 cm, n=50 (Patent Document 23), and Q=31 kg/hr, and the amount of diphenyl carbonate produced has not exceeded approximately 6.7 kg/hr, which is not an amount produced on an industrial scale.

DISCLOSURE OF THE INVENTION

It is an object of the present invention to provide, for the case of continuously producing aromatic carbonates containing a diaryl carbonate as a main product by taking an alkyl aryl carbonate as a starting material, which is obtainable through a transesterification reaction between a dialkyl carbonate and an aromatic monohydroxy compound, using a continuous multi-stage distillation column in which a catalyst is present, and continuously feeding the starting material into the continuous multi-stage distillation column, a specific process that enables the diaryl carbonate to be produced with high selectivity and high productivity stably for a prolonged period of time on an industrial scale of not less than 1 ton per hour.

Since the present inventors disclosed a process for producing aromatic carbonates using a continuous multi-stage distillation column, various proposals regarding processes for the production of aromatic carbonates by means of a reactive distillation method have been made. However, these have all been on a small scale and short operating time laboratory level, and there have been no disclosures whatsoever on a specific process or apparatus enabling mass production on an industrial scale. In view of these circumstances, the present inventors carried out studies aimed at discovering a specific process enabling a diaryl carbonate to be produced with high selectivity and high productivity stably for a prolonged period of time on an industrial scale of not less than 1 ton per hour. As a result, the present inventors have reached to the present invention.

That is, in the first aspect of the present invention, there is provided:

1. A process for the production of an aromatic carbonate containing a diaryl carbonate as a main product from a starting material comprising an alkyl aryl carbonate, which is obtainable through a transesterification reaction between a dialkyl carbonate and an aromatic monohydroxy compound, which comprises the steps of:

(i) continuously feeding said starting material into a continuous multi-stage distillation column in which a catalyst is present;

(ii) carrying out the reaction in the column to produce a dialkyl carbonate and the diaryl carbonate;

(iii) continuously withdrawing a low boiling point reaction mixture containing said produced the dialkyl carbonate from an upper portion of the column in a gaseous form and continuously withdrawing a high boiling point reaction mixture containing the diaryl carbonate from a lower portion of the column in a liquid form, wherein said continuous multi-stage distillation column comprises a structure having a pair of end plates above and below a cylindrical trunk portion having a length L (cm) and an inside diameter D (cm), and having an internal with a number of stages n thereinside, and comprises a gas outlet having an inside diameter $d_1$ (cm) at the top of the column or in an upper portion of the column near to the top, a liquid outlet having an inside diameter $d_2$ (cm) at the bottom of the column or in a lower portion of the column near to the bottom, at least one inlet provided in the upper portion and/or a middle portion of the column below the gas outlet, and at least one inlet provided in the lower portion of the column above the liquid outlet, wherein (1) said length L (cm) satisfies the following formula (1), $$1500 \leq L \leq 8000 \qquad (1),$$

(2) said inside diameter D (cm) of the column satisfies the following formula (2), $$100 \leq D \leq 2000 \qquad (2),$$

(3) a ratio of said length L (cm) to said inside diameter D (cm) of the column satisfies the following formula (3), $$2 \leq L/D \leq 40 \qquad (3),$$

(4) said number of stages n satisfies the following formula (4), $$10 \leq n \leq 80 \qquad (4),$$

(5) a ratio of said inside diameter D (cm) of the column to said inside diameter $d_1$ (cm) of the gas outlet satisfies the following formula (5), $$2 \leq D/d_1 \leq 15 \qquad (5), \text{ and}$$

(6) a ratio of said inside diameter D (cm) of the column to said inside diameter $d_2$ (cm) of the liquid outlet satisfies the following formula (6), $$5 \leq D/d_2 \leq 30 \qquad (6).$$

2. The process according to item 1, wherein distillation is carried out simultaneously in said step (ii), 3. The process according to claim 1 or 2, wherein said aromatic carbonate containing the diaryl carbonate as the main product is continuously produced and an amount of said diaryl carbonate produced is not less than 1 ton per hour.

In another aspect of the process according to the present invention, there is provided:

4. In a process for the production of an aromatic carbonate containing a diaryl carbonate as a main product in which the aromatic carbonate containing the diaryl carbonate as the main product is produced continuously by continuously feeding an alkyl aryl carbonate as a starting material, which is obtainable through a transesterification reaction between a dialkyl carbonate and an aromatic monohydroxy compound, into a continuous multi-stage distillation column in which a catalyst is present, carrying out the reaction and the distillation simultaneously in the column, continuously withdrawing a low boiling point reaction mixture containing a produced dialkyl carbonate from an upper portion of the column in a gaseous form, and continuously withdrawing a high boiling point reaction mixture containing the diary carbonate from a lower portion of the column in a liquid form, the improvement in which said continuous multi-stage distillation column comprises a structure having a pair of end plates above and below a cylindrical trunk portion having a length L (cm) and an inside diameter D (cm), and having an internal with a number of stages n thereinside, and comprises a gas outlet having an inside diameter $d_1$ (cm) at the top of the column or in an upper portion of the column near to the top, a liquid outlet having an inside diameter $d_2$ (cm) at the bottom of the column or in a lower portion of the column near to the bottom, at least one inlet provided in the upper portion and/or a middle portion of the column below the gas outlet, and at least one inlet provided in the lower portion of the column above the liquid outlet, wherein (1) said length L (cm) satisfies the following formula (1), $$1500 \leq L \leq 8000 \quad (1),$$

(2) said inside diameter D (cm) of the column satisfies the following formula (2), $$100 \leq D \leq 2000 \quad (2),$$

(3) a ratio of said length L (cm) to said inside diameter D (cm) of the column satisfies the following formula (3), $$2 \leq L/D \leq 40 \quad (3),$$

(4) said number of stages n satisfies the following formula (4), $$10 \leq n \leq 80 \quad (4),$$

(5) a ratio of said inside diameter D (cm) of the column to said inside diameter $d_1$ (cm) of the gas outlet satisfies the following formula (5), $$2 \leq D/d_1 \leq 15 \quad (5), \text{ and}$$

(6) a ratio of said inside diameter D (cm) of the column to said inside diameter $d_2$ (cm) of the liquid outlet satisfies the following formula (6), $$5 \leq D/d_2 \leq 30 \quad (6),$$

5. The process according to item 4, wherein an amount of the diary carbonate produced is not less than 1 ton per hour, 6. The process according to any one of items 1 to 5, wherein $d_1$ and $d_2$ satisfy the following formula (7)

$$1 \leq d_1/d_2 \leq 6 \quad (7),$$

7. The process according to any one of items 1 to 6, wherein L, D, L/D, n, $D/d_1$, and $D/d_2$ for said continuous multi-stage distillation column satisfy the following formulae; $2000 \leq L \leq 6000$, $150 \leq D \leq 1000$, $3 \leq L/D \leq 30$, $15 \leq n \leq 60$, $2.5 \leq D/d_1 \leq 12$, and $7 \leq D/d_2 \leq 25$, respectively, 8. The process according to any one of items 1 to 7, wherein L, D, L/D, n, $D/d_1$, and $D/d_2$ for the continuous multi-stage distillation column satisfy the following formulae; $2500 \leq L \leq 5000$, $200 \leq D \leq 800$, $5 \leq L/D \leq 15$, $20 \leq n \leq 50$, $3 \leq D/d_1 \leq 10$, and $9 \leq D/d_2 \leq 20$, respectively, 9. The process according to any of items 1 to 8, wherein said continuous multi-stage distillation column is a distillation column having a packing and a tray as the internal, 10. The process according to item 9, wherein said continuous multi-stage distillation column is a distillation column having, as the internal, the packing in the upper portion of the column, and the tray in the lower portion of the column, 11. The process according to item 9 or 10, wherein said packing of the internal is a structured packing, 12. The process according to item 9 or 10, wherein said tray of the internal is a sieve tray having a sieve portion and a down comer portion, 13. The process according to item 9 or 10, wherein said packing of the internal is one or more of the structured packing, and said trays is a sieve tray having a sieve portion and a down comer portion, 14. The process according to item 11 or 13, wherein said structured packing is at least one selected from the group consisting of Mellapak, Gempak, TECHNO-PAK, FLEXI-PAK, a Sulzer packing, a Goodroll packing and a Glitchgrid, 15. The process according to item 12 or 13, wherein said sieve tray has 100 to 1000 holes/$m^2$ in the sieve portion, 16. The process according to any one of items 12, 13 or 15, wherein the cross-sectional area per hole of said sieve tray is in a range of from 0.5 to 5 $cm^2$, 17. The process according to item 13, wherein said structured packing is at least one selected from the group consisting of Mellapak, Gempak, TECHNO-PAK, FLEXI-PAK, a Sulzer packing, a Goodroll packing and a Glitchgrid, aid sieve tray has 100 to 1000 holes/$m^2$ in the sieve portion, and the cross-sectional area per hole of said sieve tray is in a range of from 0.5 to 5 $cm^2$.

In the second aspect of the present invention, there is provided:

18. An aromatic carbonate comprising a halogen content of not more than 0.1 ppm, produced by the process according to any one of items 1 to 17.

In the third aspect of the present invention, there is provided:

19. A continuous multi-stage distillation column for carrying out reaction and distillation, comprising:

a cylindrical trunk portion having a length L (cm) and an inside diameter D (cm);

a pair of end plates provided above and below the trunk portion;

an internal with a number of stages n inside the trunk portion;

a gas outlet which has an inside diameter $d_1$ (cm) and which being provided on the end plate at the top of the column or in an upper portion of the column near thereto;

a liquid outlet which has an inside diameter $d_2$ (cm) and which being provided on the end plate at the bottom of the column or in a lower portion of the column near thereto;

at least one inlet provided in the upper portion and/or a middle portion of the column below the gas outlet; and at least one inlet provided in the lower portion of the column above the liquid outlet, wherein (1) said length L (cm) satisfies the following formula (1), $$1500 \leq L \leq 8000 \quad (1),$$

(2) said inside diameter D (cm) of the column satisfies the following formula (2), $$100 \leq D \leq 2000 \quad (2),$$

(3) a ratio of said length L (cm) to said inside diameter D (cm) of the column satisfies the following formula (3), $$2 \leq L/D \leq 40 \quad (3),$$

(4) said number of stages n satisfies the following formula (4), $$10 \leq n \leq 80 \quad (4),$$

(5) a ratio of said inside diameter D (cm) of the column to said inside diameter $d_1$ (cm) of the gas outlet satisfies the following formula (5), $$2 \leq D/d_1 \leq 15 \quad (5), \text{ and}$$

(6) a ratio of said inside diameter D (cm) of the column to said inside diameter $d_2$ (cm) of the liquid outlet satisfies the following formula (6), $$5 \leq D/d_2 \leq 30 \quad (6),$$

20. The continuous multi-stage distillation column according to item 19, wherein $d_1$ and $d_2$ satisfy the following formula (7)

$$1 \leq d_1/d_2 \leq 6 \quad (7).$$

21. The continuous multi-stage distillation column according to item 19 or 20, wherein L, D, L/D, n, $D/d_1$, and $D/d_2$ for said continuous multi-stage distillation column satisfy the following formulae; $2000 \leq L \leq 6000$, $150 \leq D \leq 1000$, $3 \leq L/D \leq 30$, $15 \leq n \leq 60$, $2.5 \leq D/d_1 \leq 12$, and $7 \leq D/d_2 \leq 25$, respectively, 22. The continuous multi-stage distillation column according to any one of items 19 to 21, wherein L, D, L/D, n, $D/d_1$, and $D/d_2$ for the continuous multi-stage distillation column satisfy the following formulae; $2500 \leq L \leq 5000$, $200 \leq D \leq 800$, $5 \leq L/D \leq 15$, $20 \leq n \leq 50$, $3 \leq D/d_1 \leq 10$, and $9 \leq D/d_2 \leq 20$, respectively, 23. The continuous multi-stage distillation column according to any one of items 19 to 22, wherein said continuous multi-stage distillation column is a distillation column having a packing and a tray as the internal, 24. The continuous multi-stage distillation column according to items 23, wherein said continuous multi-stage distillation column is a distillation column having, as the internal, the packing in the upper portion of the column, and the tray in the lower portion of the column, 25. The continuous multi-stage distillation column according to item 23 or 24, wherein said packing of the internal is a structured packing, 26. The continuous multi-stage distillation column according to item 23 or 24, wherein said tray of the internal is a sieve tray having a sieve portion and a down comer portion, 27. The continuous multi-stage distillation column according to item 23 or 24, wherein said packing of the internal is one or more of the structured packing, and said trays is a sieve tray having a sieve portion and a down comer portion.

28. The continuous multi-stage distillation column according to item 25 or 27, wherein said structured packing is at least one selected from the group consisting of Mellapak, Gempak, TECHNO-PAK, FLEXI-PAK, a Sulzer packing, a Goodroll packing and a Glitchgrid, 29. The continuous multi-stage distillation column according to item 26 or 27, wherein said sieve tray has 100 to 1000 holes/m² in the sieve portion, 30. The continuous multi-stage distillation column according to any one of items 26, 27 or 29, wherein the cross-sectional area per hole of said sieve tray is in a range of from 0.5 to 5 cm², 31. The continuous multi-stage distillation column according to item 27, wherein said structured packing is at least one selected from the group consisting of Mellapak, Gempak, TECHNO-PAK, FLEXI-PAK, a Sulzer packing, a Goodroll packing and a Glitchgrid, aid sieve tray has 100 to 1000 holes/m² in the sieve portion, and the cross-sectional area per hole of said sieve tray is in a range of from 0.5 to 5 cm².

ADVANTAGEOUS EFFECTS OF THE INVENTION

It has been discovered that according to the present invention, taking an alkyl aryl carbonate as a starting material, which is obtainable from a dialkyl carbonate and an aromatic monohydroxy compound, a diaryl carbonate can be produced on an industrial scale of not less than 1 ton per hour, preferably not less than 2 tons per hour, more preferably not less than 3 tons per hour, with a high selectivity of not less than 95%, preferably not less than 97%, more preferably not less than 99%, stably for a prolonged period of time of not less than 2000 hours, preferably not less than 3000 hours, more preferably not less than 5000 hours. A diaryl carbonate obtained by subjecting the aromatic carbonates containing the diaryl carbonate as a main component obtained through the present invention to separation/purification through distillation or the like is of high purity, and is useful as a raw material of a transesterification method polycarbonate or polyester carbonate or the like, or as a raw material of a non-phosgene method isocyanate or urethane or the like. Moreover, according to the present invention, because a starting material and catalyst not containing a halogen are generally used, the diaryl carbonate obtained has a halogen content of not more than 0.1 ppm, preferably not more than 10 ppb, more preferably not more than 1 ppb.

DESCRIPTION OF REFERENCE NUMERALS

Figure 1:
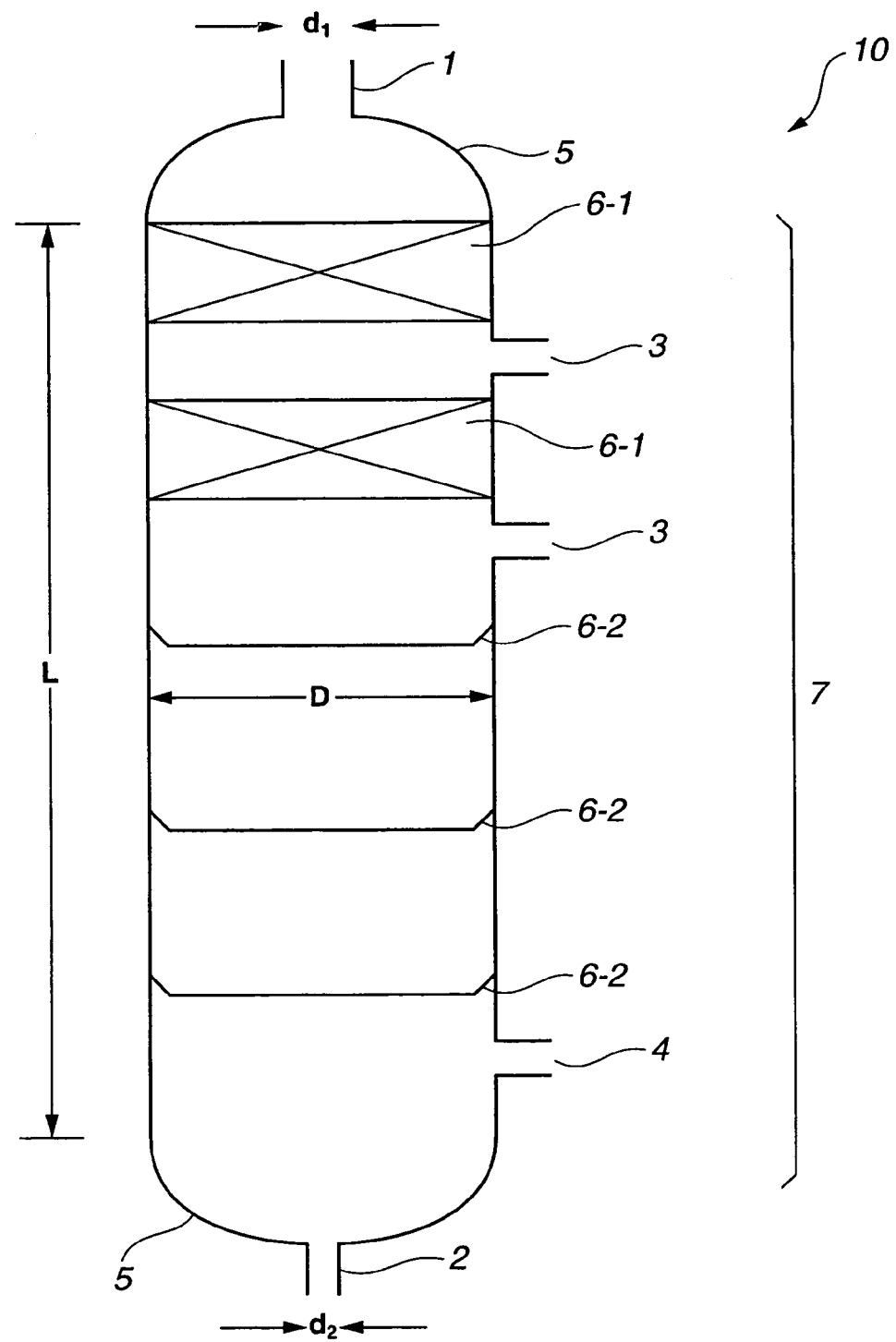
FIG. 1 is a schematic view of the continuous multi-stage distillation column for carrying out the present invention, the distillation column having an internal provided inside a trunk portion thereof.

1: gas outlet, 2: liquid outlet, 3: inlet, 4: inlet, 5: end plate, 6-1: internal (packing), 6-2: internal (tray), 7: trunk portion, 10: continuous multi-stage distillation column, L: length of trunk portion (cm), D: inside diameter of trunk portion (cm), $d_1$: Inside diameter of gas outlet (cm), $d_2$: Inside diameter of liquid outlet (cm)

BEST MODE FOR CARRYING OUT THE INVENTION

In the following, the present invention is described in detail.

A dialkyl carbonate used for obtaining an alkyl aryl carbonate that is a starting material of the present invention is a compound represented by general formula (8).

$$R^1OCOOR^1 \tag{8}$$

wherein $R^1$ represents an alkyl group having 1 to 10 carbon atoms, an alicyclic group having 3 to 10 carbon atoms, or an aralkyl group having 6 to 10 carbon atoms. Examples of $R^1$ include alkyl groups such as methyl, ethyl, propyl (isomers), allyl, butyl (isomers), butenyl (isomers), pentyl (isomers), hexyl (isomers), heptyl (isomers), octyl (isomers), nonyl (isomers), decyl (isomers) and cyclohexylmethyl; alicyclic groups such as cyclopropyl, cyclobutyl, cyclopentyl, cyclohexyl and cycloheptyl; and aralkyl groups such as benzyl, phenethyl (isomers), phenylpropyl (isomers), phenylbutyl (isomers) and methylbenzyl (isomers). The above-mentioned alkyl groups, alicyclic groups and aralkyl groups may be substituted with other substituents such as a lower alkyl group, a lower alkoxy group, a cyano group or a halogen atom, and may also contain an unsaturated bond.

Examples of dialkyl carbonates having such $R^1$ include dimethyl carbonate, diethyl carbonate, dipropyl carbonate (isomers), diallyl carbonate, dibutenyl carbonate (isomers), dibutyl carbonate (isomers), dipentyl carbonate (isomers), dihexyl carbonate (isomers), diheptyl carbonate (isomers), dioctyl carbonate (isomers), dinonyl carbonate (isomers), didecyl carbonate (isomers), dicyclopentyl carbonate, dicyclohexyl carbonate, dicycloheptyl carbonate, dibenzyl carbonate, diphenethyl carbonate (isomers), di(phenylpropyl) carbonate (isomers), di(phenylbutyl) carbonate (isomers), di(chlorobenzyl) carbonate (isomers), di(methoxybenzyl) carbonate (isomers), di(methoxymethyl) carbonate, di(methoxyethyl) carbonate (isomers), di(chloroethyl) carbonate (isomers) and di(cyanoethyl) carbonate (isomers).

Of these dialkyl carbonates, ones preferably used in the present invention are dialkyl carbonates in which $R^1$ is an alkyl group having not more than four carbon atoms and not containing a halogen atom. A particularly preferable one is dimethyl carbonate. Moreover, of preferable dialkyl carbonates, particularly preferable ones are dialkyl carbonates produced in a state substantially not containing a halogen atom, for example, ones produced from an alkylene carbonate substantially not containing a halogen atom and an alcohol substantially not containing a halogen atom.

An aromatic monohydroxy compound used in the present invention is a compound represented by undermentioned general formula (9). The type of the aromatic monohydroxy compound is not limited, so long as the hydroxyl group is directly bonded to the aromatic group;

$$Ar^1OH \tag{9}$$

wherein $Ar^1$ represents an aromatic group having 5 to 30 carbon atoms. Examples of aromatic monohydroxy compounds having such $Ar^1$ include phenol; various alkylphenols such as cresol (isomers), xylenol (isomers), trimethylphenol (isomers), tetramethylphenol (isomers), ethylphenol (isomers), propylphenol (isomers), butylphenol (isomers), diethylphenol (isomers), methylethylphenol (isomers), methylpropylphenol (isomers), dipropylphenol (isomers), methylbutylphenol (isomers), pentylphenol (isomers), hexylphenol (isomers) and cyclohexylphenol (isomers); various alkoxyphenols such as methoxyphenol (isomers) and ethoxyphenol (isomers); arylalkylphenols such as phenylpropylphenol (isomers); naphthol (isomers) and various substituted naphthols; and heteroaromatic monohydroxy compounds such as hydroxypyridine (isomers), hydroxycoumarin (isomers) and hydroxyquinoline (isomers).

Of these aromatic monohydroxy compounds, ones preferably used in the present invention are aromatic monohydroxy compounds in which $Ar^1$ is an aromatic group having 6 to 10 carbon atoms. Phenol is particularly preferable. Moreover, of these aromatic monohydroxy compounds, ones substantially not containing a halogen are preferably used in the present invention.

The molar ratio of the dialkyl carbonate to the aromatic monohydroxy compound used for obtaining the alkyl aryl carbonate that is the starting material of the present invention must be in a range of from 0.4 to 4. Outside this range, an amount of unreacted material remaining, based on a prescribed amount of the alkyl aryl carbonate produced becomes high, which is not efficient for the production of the aromatic carbonate. Moreover, much energy is required to recover the alkyl aryl carbonate. For such reasons, the above molar ratio is preferably in a range of from 0.5 to 3.0, more preferably 0.8 to 2.5, yet more preferably from 1.0 to 2.0.

In the present invention, not less than 1 ton per hour of the diaryl carbonate is produced continuously. The minimum amount of the alkyl aryl carbonate fed in continuously for the above production is generally 5 P ton/hr, preferably 3 P ton/hr, more preferably 2 P ton/hr, based on the amount of the diaryl carbonate (P ton/hr) to be produced. More preferably, this amount can be made to be less than 1.8 P ton/hr.

The aromatic carbonates produced in the present invention are aromatic carbonates containing as a main component a diaryl carbonate obtained through a transesterification reaction of the alkyl aryl carbonate. Included under this transesterification reaction are a reaction in which the alkoxy group of the alkyl aryl carbonate is exchanged with the aryloxy group of the aromatic monohydroxy compound present in the reaction system so as to eliminate an alcohol, and a reaction in which two molecules of the alkyl aryl carbonate are converted into the diaryl carbonate and the dialkyl carbonate through a transesterification reaction therebetween, i.e. a disproportionation reaction. In the present invention, it is mainly the disproportionation reaction of the alkyl aryl carbonate that occurs. Moreover, in the present invention, a starting material and catalyst not containing a halogen atom at all can be used. In this case, the produced aromatic carbonates containing the diaryl carbonate as the main component thereof does not contain a halogen at all, and hence it is important as the raw material when industrially producing a polycarbonate by means of a transesterification method. That is, the diaryl carbonate obtained by subjecting the aromatic carbonates containing the diaryl carbonate as the main component obtained according to the present invention to separation/purification through distillation or the like is of high purity and does not contain a halogen at all, and hence it is very useful as a raw material for the production of an aromatic polycarbonate through a transesterification method with an aromatic dihydroxy compound.

The alkyl aryl carbonate used as the starting material of the present invention may be of high purity, or may contain other compounds, for example may contain the dialkyl carbonate and/or the aromatic monohydroxy compound used for obtaining the alkyl aryl carbonate, or may contain compounds or reaction by-products produced in this process and/or another process, for example an alcohol, an alkyl aryl ether, and/or a diaryl carbonate. A method in which the dialkyl carbonate/ aromatic monohydroxy compound transesterification reaction mixture is taken as the starting material in the present invention without unreacted material or the catalyst being separated therefrom is also preferable. Moreover, in the case of industrial implementation as in the present invention, as the dialkyl carbonate and aromatic monohydroxy compound used for obtaining the alkyl aryl carbonate that is the starting material of the present invention, besides fresh dialkyl carbonate and aromatic monohydroxy compound newly introduced into the reaction system, it is also preferable to use dialkyl carbonate and aromatic monohydroxy compound recovered from this process and/or another process.

As a catalyst used in the present invention, for example, a metal-containing compound selected from the following compounds can be used. This catalyst may be the same as the catalyst used for obtaining the alkyl aryl carbonate that is the starting material. Preferably, the catalyst that has been used in the reaction between the dialkyl carbonate and the aromatic monohydroxy compound can be used as is without being separated out.

<Lead Compounds>

Lead oxides such as PbO, $PbO_2$ and $Pb_3O_4$; lead sulfides such as PbS and $Pb_2S$; lead hydroxides such as $Pb(OH)_2$ and $Pb_2O_2(OH)_2$; plumbites such as $Na_2PbO_2$, $K_2PbO_2$, $NaHPbO_2$ and $KHPbO_2$; plumbates such as $Na_2PbO_3$, $Na_2H_2PbO_4$, $K_2PbO_3$, $K_2[Pb(OH)_6]$, $K_4PbO_4$, $Ca_2PbO_4$ and $CaPbO_3$; lead carbonates and basic salts thereof such as $PbCO_3$ and $2PbCO_3.Pb(OH)_2$; lead salts of organic acids, and carbonates and basic salts thereof, such as $Pb(OCOCH_3)_2$, $Pb(OCOCH_3)_4$ and $Pb(OCOCH_3)_2.PbO.3H_2O$, organolead compounds such as $Bu_4Pb$, $Ph_4Pb$, $Bu_3PbCl$, $Ph_3PbBr$, $Ph_3Pb$ (or $Ph_6Pb_2$), $Bu_3PbOH$ and $Ph_3PbO$ (wherein Bu represents a butyl group, and Ph represents a phenyl group); alkoxylead compounds and aryloxylead compounds such as $Pb(OCH_3)_2$, $(CH_3O)Pb(OPh)$ and $Pb(OPh)_2$; lead alloys such as Pb—Na, Pb—Ca, Pb—Ba, Pb—Sn and Pb—Sb; lead minerals such as galena and zinc blende; and hydrates of such lead compounds;

<Copper family Metal Compounds>

Salts and complexes of copper family metals such as CuCl, $CuCl_2$, CuBr, $CuBr_2$, CuI, $CuI_2$, $Cu(OAc)_2$, $Cu(acac)_2$, copper oleate, $Bu_2Cu$, $(CH_3O)_2Cu$, $AgNO_3$, AgBr, silver picrate, $AgC_6H_6ClO_4$, $[AuC\equiv C-C(CH_3)_3]n$ and $[Cu(C_7H_8)Cl]_4$ (wherein acac represents an acetylacetone chelate ligand);

<Alkali Metal Complexes>

Alkali metal complexes such as Li(acac) and $LiN(C_4H_9)_2$;

<Zinc Complexes>

Zinc complexes such as $Zn(acac)_2$;

<Cadmium Complexes>

Cadmium complexes such as $Cd(acac)_2$;

<Iron Family Metal Compounds>

Complexes of iron family metals such as $Fe(C_{10}H_8)(CO)_5$, $Fe(CO)_5$, $Fe(C_4H_6)(CO)_3$, $Co(mesitylene)_2$, $(PEt_2Ph)_2$, $COC_5F_5(CO)_7$, $Ni-\pi-C_5H_5NO$ and ferrocene;

<Zirconium Complexes>

Zirconium complexes such as $Zr(acac)_4$ and zirconocene;

<Lewis Acid Type Compounds>

Lewis acids and Lewis acid-forming transition metal compounds such as $AlX_3$, $TiX_3$, $TiX_4$, $VOX_3$, $VX_5$, $ZnX_2$, $FeX_3$ and $SnX_4$ (wherein X represents a halogen atom, an acetoxy group, an alkoxy group or an aryloxy group); and <Organo-tin Compounds>

Organo-tin compounds such as $(CH_3)_3SnOCOCH_3$, $(C_2H_5)_3SnOCOC_6H_5$, $Bu_3SnOCOCH_3$, $Ph_3SnOCOCH_3$, $Bu_2Sn(OCOCH_3)_2$, $Bu_2Sn(OCOC_{11}H_{23})_2$, $Ph_3SnOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(OCH_3)_2$, $(C_2H_5)_3SnOH$, $Ph_3SnOH$, $Bu_2SnO$, $(C_8H_{17})_2SnO$, $Bu_2SnCl_2$ and $BuSnO(OH)$.

Each of these catalysts may be a solid catalyst fixed inside the multi-stage distillation column, or may be a soluble catalyst that dissolves in the reaction system.

Each of these catalyst components may of course have been reacted with an organic compound present in the reaction system such as an aliphatic alcohol, the aromatic monohydroxy compound, the alkyl aryl carbonate, the diaryl carbonate or the dialkyl carbonate, or may have been subjected to heating treatment with the starting material or products prior to the reaction.

In the case of carrying out the present invention with a soluble catalyst that dissolves in the reaction system, the catalyst is preferably one having a high solubility in the reaction liquid under the reaction conditions. Examples of preferable catalysts in this sense include PbO, $Pb(OH)_2$ and $Pb(OPh)_2$; $TiCl_4$, $Ti(OMe)_4$, $(MeO)Ti(OPh)_3$, $(MeO)_2Ti(OPh)_2$, $(MeO)_3Ti(OPh)$ and $Ti(OPh)_4$; $SnCl_4$, $Sn(OPh)_4$, $Bu_2SnO$ and $Bu_2Sn(OPh)_2$; $FeCl_3$, $Fe(OH)_3$ and $Fe(OPh)_3$; and such catalysts that have been treated with phenol, the reaction liquid or the like.

FIG. 1 shows a schematic view of the continuous multi-stage distillation column for carrying out the present invention. The continuous multi-stage distillation column 10 used in the present invention comprises a structure having a pair of end plates 5 above and below a cylindrical trunk portion 7 having a length L (cm) and an inside diameter D (cm), and having an internal 6 (6-1: packing; 6-2: tray) with a number of stages n thereinside, and has a gas outlet 1 having an inside diameter $d_1$ (cm) at the top of the column or in an upper portion of the column near to the top, a liquid outlet 2 having an inside diameter $d_2$ (cm) at the bottom of the column or in a lower portion of the column near to the bottom, at least one inlet 3 provided in the upper portion and/or a middle portion of the column below the gas outlet, and at least one inlet 4 provided in the lower portion of the column above the liquid outlet. Note that since FIG. 1 shows one embodiment of the continuous multi-stage distillation column according to the present invention, an arrangement of the internal is not limited to that of FIG. 1.

Moreover the continuous multi-stage distillation column 10 according to the present invention must be made to satisfy various conditions so as to be able to carry out not only distillation but also reaction at the same time so as to be able to produce not less than 1 ton of the diaryl carbonate per hour stably for a prolonged period of time. That is, the continuous multi-stage distillation column 10 according to the present invention satisfies not only conditions from the perspective of the distillation function, but rather these conditions are combined with conditions required so as make the reaction proceed stably and with high selectivity.

More specifically, the following are required for the continuous multi-stage distillation column according to the present invention:

(1) the length L (cm) must satisfy formula (1), $$1500 \leq L \leq 8000 \qquad (1),$$

(2) the inside diameter D (cm) of the column must satisfy formula (2), $$100 \leq D \leq 2000 \qquad (2),$$

(3) the ratio of the length L (cm) to the inside diameter D (cm) of the column must satisfy formula (3), $$2 \leq L/D \leq 40 \qquad (3),$$

(4) the number of stages n must satisfy formula (4), $$10 \leq n \leq 80 \qquad (4),$$

(5) the ratio of the inside diameter D (cm) of the column to the inside diameter $d_1$ (cm) of the gas outlet must satisfy formula (5), $$2 \leq D/d_1 \leq 15 \qquad (5), \text{ and}$$

(6) the ratio of the inside diameter D (cm) of the column to the inside diameter $d_2$ (cm) of the liquid outlet must satisfy formula (6), $$5 \leq D/d_2 \leq 30 \qquad (6).$$

It should be noted that the term "in an upper portion of the column near to the top" refers to the portion extending downwardly from the top of the column to the location measuring about 0.25 L, and the term "in a lower portion of the column near to the bottom" refers to the portion extending upwardly from the bottom of the column to the location measuring about 0.25 L. Note that L is defined above.

It has been discovered that by using the continuous multi-stage distillation column that simultaneously satisfies formulae (1), (2), (3), (4), (5) and (6), when producing aromatic carbonates containing the diaryl carbonate as the main component thereof from an alkyl aryl carbonate, the diaryl carbonate can be produced on an industrial scale of not less than 1 ton per hour with high selectivity and high productivity stably for a prolonged period of time, for example not less than 2000 hours, preferably not less than 3000 hours, more preferably not less than 5000 hours. The reason why it has become possible to produce the aromatic carbonates on an industrial scale with such excellent effects by implementing the process according to the present invention is not clear, but this is supposed to be due to a combined effect brought about when the conditions of the formulae (1) to (6) are combined. Preferable ranges for the respective factors are described below.

If L (cm) is less than 1500, then the conversion decreases and it is not possible to attain the desired production amount. Moreover, to keep down the equipment cost while securing the conversion enabling the desired production amount to be attained, L must be made to be not more than 8000. A more preferable range for L (cm) is $2000 \leq L \leq 6000$, with $2500 \leq L \leq 5000$ being yet more preferable.

If D (cm) is less than 100, then it is not possible to attain the desired production amount. Moreover, to keep down the equipment cost while attaining the desired production amount, D must be made to be not more than 2000. A more preferable range for D (cm) is $150 \leq D \leq 1000$, with $200 \leq D \leq 800$ being yet more preferable.

If L/D is less than 2 or greater than 40, then stable operation becomes difficult. In particular, if L/D is greater than 40, then the pressure difference between the top and bottom of the column becomes too great, and hence prolonged stable operation becomes difficult. Moreover, it is necessary to increase the temperature in the lower portion of the column, and hence side reactions become liable to occur, thereby bringing about a decrease in the selectivity. A more preferable range for L/D is $3 \leq L/D \leq 30$, with $5 \leq L/D \leq 15$ being yet more preferable.

If n is less than 10, then the conversion decreases and it is not possible to attain the desired production amount. Moreover, to keep down the equipment cost while securing the conversion enabling the desired production amount to be attained, n must be made to be not more than 80. Furthermore, if n is greater than 80, then the pressure difference between the top and bottom of the column becomes too great, and hence prolonged stable operation becomes difficult. Moreover, it is necessary to increase the temperature in the lower portion of the column, and hence side reactions become liable to occur, thereby bringing about a decrease in the selectivity. A more preferable range for n is $15 \leq n \leq 60$, with $20 \leq n \leq 50$ being yet more preferable.

If $D/d_1$ is less than 2, then the equipment cost becomes high. Moreover, large amounts of gaseous components are readily released to the outside of the system, and hence stable operation becomes difficult. If $D/d_1$ is greater than 15, then the gaseous component withdrawal amount becomes relatively low, and hence stable operation becomes difficult, and moreover a decrease in the conversion is brought about. A more preferable range for $D/d_1$ is $2.5 \leq D/d_1 \leq 12$, with $3 \leq D/d_1 \leq 10$ being yet more preferable.

If $D/d_2$ is less than 5, then the equipment cost becomes high. Moreover, the liquid withdrawal amount becomes relatively high, and hence stable operation becomes difficult. If $D/d_2$ is greater than 30, then the flow rate through the liquid outlet and piping becomes excessively fast, and hence erosion becomes liable to occur, thereby bringing about corrosion of the apparatus. A more preferable range for $D/d_2$ is $7 \leq D/d_2 \leq 25$, with $9 \leq D/d_2 \leq 20$ being yet more preferable.

Furthermore, it has been found that in the present invention it is further preferable for $d_1$ and $d_2$ to satisfy formula (7):

$$1 \leq d_1/d_2 \leq 6 \qquad (7).$$

The term "prolonged stable operation" used in the present invention means that operation can be carried out continuously in a steady state based for not less than 1000 hours, preferably not less than 3000 hours, more preferably not less than 5000 hours without clogging of piping, erosion and so on, and a prescribed amount of the diaryl carbonate can be produced while maintaining high selectivity.

A characteristic feature of the present invention is that the diaryl carbonate can be produced stably for a prolonged period of time with high selectivity and with a high productivity of not less than 1 ton per hour, preferably not less than 2 tons per hour, more preferably not less than 3 tons per hour. Moreover, another characteristic feature of the present invention is that in the case that L, D, L/D, n, $D/d_1$, and $D/d_2$ for the continuous multi-stage distillation column satisfy the following formulae: $2000 \leq L \leq 6000$, $150 \leq D \leq 1000$, $3 \leq L/D \leq 30$, $15 \leq n \leq 60$, $2.5 \leq D/d_1 \leq 12$, and $7 \leq D/d_2 \leq 25$, respectively, not less than 2 tons per hour, preferably not less than 2.5 tons per hour, more preferably not less than 3 tons per hour of the diaryl carbonate can be produced. Furthermore, another characteristic feature of the present invention is that in the case that L, D, L/D, n, $D/d_1$, and $D/d_2$ for the continuous multi-stage distillation column satisfy the following formulae: $2500 \leq L \leq 5000$, $200 \leq D \leq 800$, $5 \leq L/D \leq 15$, $20 \leq n \leq 50$, $3 \leq D/d_1 \leq 10$, and $9 \leq D/d_2 \leq 20$, respectively, not less than 3 tons per hour, preferably not less than 3.5 tons per hour, more preferably not less than 4 tons per hour of the diaryl carbonate can be produced.

"Selectivity for the diaryl carbonate" used in the present invention is based on the alkyl aryl carbonate reacted. In the present invention, a high selectivity of not less than 95% can generally be attained, preferably not less than 97%, more preferably not less than 99%.

The continuous multi-stage distillation column according to the present invention is preferably a distillation column having a tray and/or a packing as the internal. The term "internal" used in the present invention means the part in the distillation column where gas and liquid are actually brought into contact with one another. As the tray, for example, a bubble-cap tray, a sieve tray, a valve tray, a counterflow tray, a Superfrac tray, a Maxfrac tray, or the like are preferable. As the packing, a random packing such as a Raschig ring, a Lessing ring, a Pall ring, a Berl saddle, an Intalox saddle, a Dixon packing, a McMahon packing or Heli-Pak, or a structured packing such as Mellapak, Gempak, TECHNO-PAK, FLEXI-PAK, a Sulzer packing, a Goodroll packing and a Glitchgrid are preferable. The multi-stage column having both a tray portion and a portion packed with a packing can also be used. Note that the term "number of stages (n) of an internal" used in the present invention means that the total number of trays in the case of a tray, and the theoretical number of stages in the case of a packing. Therefore, in the case of the multi-stage column having both the tray portion and the portion packed with the packing, n means the sum of the total number of trays and the theoretical number of stages of the packing.

The reaction between the alkyl aryl carbonate and the aromatic monohydroxy compound present in the reaction system in the present invention has an extremely low equilibrium constant, and moreover the reaction rate is slow. Furthermore, the disproportionation reaction of the alkyl aryl carbonate that is the main reaction is also an equilibrium reaction, and has a low equilibrium constant, and the reaction rate thereof is slow. It has been discovered that the multi-stage distillation column having both the packing and the tray as the internal is preferable as the continuous multi-stage distillation column used in the reactive distillation for carrying out these reactions in the present invention. It is more preferable for this distillation column to have a portion packed with the packing provided in the upper portion of the distillation column, and a tray portion provided in the lower portion of the distillation column. Moreover, in the present invention, the packing is preferably the structured packing, it further being preferable to use one or more thereof. The structured packing is preferably of at least one type selected from the group consisting of Mellapak, Gempak, TECHNO-PAK, FLEXI-PAK, a Sulzer packing, a Goodroll packing and a Glitchgrid.

Furthermore, it has been discovered that for the continuous multi-stage distillation column according to the present invention, a sieve tray having a sieve portion and a down comer portion is particularly preferable as the tray of the internal in terms of the relationship between performance and equipment cost. It has also been discovered that the sieve tray preferably has 100 to 1000 holes/m$^2$ in the sieve portion. A more preferable number of holes is 120 to 900 holes/m$^2$, yet more preferably 150 to 800 holes/m$^2$. Moreover, it has been discovered that the cross-sectional area per hole of the sieve tray is preferably in a range of from 0.5 to 5 cm$^2$. A more preferable cross-sectional area per hole is 0.7 to 4 cm$^2$, yet more preferably 0.9 to 3 cm$^2$. Furthermore, it has been discovered that it is more preferable if the sieve tray has 100 to 1000 holes/m$^2$ in the sieve portion, and the cross-sectional area per hole is in a range of from 0.5 to 5 cm$^2$. Furthermore, it has been discovered that it is yet more preferable if the structured packing is of at least one selected from the group consisting of Mellapak, Gempak, TECHNO-PAK, FLEXI-PAK, a Sulzer packing, a Goodroll packing and a Glitchgrid, and the sieve tray has 100 to 1000 holes/m$^2$ in the sieve portion, and the cross-sectional area per hole is in a range of from 0.5 to 5 cm$^2$. It has been shown that by adding the above conditions to the continuous multi-stage distillation column, the object of the present invention can be attained more easily.

When carrying out the present invention, the diaryl carbonate can be produced continuously by continuously feeding the starting material containing the alkyl aryl carbonate into the continuous multi-stage distillation column in which the catalyst is present, carrying out the reaction and the distillation simultaneously in the column, continuously withdrawing a low boiling point reaction mixture containing the produced dialkyl carbonate and alcohol from the upper portion of the column in a gaseous form, and continuously withdrawing a high boiling point reaction mixture containing aromatic carbonates containing the diaryl carbonate as the main product therein from the lower portion of the column in a liquid form. The low boiling point reaction mixture may contain an alkyl aryl ether and the aromatic monohydroxy compound present in the system, unreacted alkyl aryl carbonate and so on. Moreover, the high boiling point reaction mixture may contain the aromatic monohydroxy compound, unreacted alkyl aryl carbonate and so on. It should be noted that, as mentioned above, in addition to the alkyl aryl carbonate, the starting material may contain the dialkyl carbonate and alcohol that are reaction products, the aromatic monohydroxy compound, the diaryl carbonate, the alkyl aryl ether, high boiling point reaction by-products and so on. Taking into consideration the equipment and cost required for separation and purification in other processes, when actually implementing the present invention industrially, it is preferable for the starting material to contain small amounts of such compounds.

Moreover, in the present invention, a process in which a reflux operation of condensing the gaseous component withdrawn from the top of the reactive distillation column, and then returning some of this component into the upper portion of the distillation column is carried out is preferable. In this case, the reflux ratio is in a range of from 0.05 to 10, preferably 0.08 to 5, more preferably 0.1 to 2. In the present invention, when continuously feeding the starting material containing the alkyl aryl carbonate into the continuous multi-stage distillation column, this starting material is preferably fed into the distillation column in a liquid form and/or a gaseous form from inlet(s) provided in one or more of the positions in the upper portion or the middle portion of the column below the gas outlet in the upper portion of the distillation column. Moreover, when using the distillation column having the packing portion in the upper portion thereof and the tray portion in the lower portion thereof, which is a preferable embodiment of the present invention, it is preferable for at least one position of the inlet to be provided between the packing portion and the tray portion. Furthermore, in the case that the packing comprises two or more of the structured packings, it is preferable for the inlet to be provided in a space between the plural structured packings.

In the present invention, the method of making the catalyst be present in the continuous multi-stage distillation column may be any method, but in the case that the catalyst is a solid that is insoluble in the reaction liquid, there is, for example, a method in which the catalyst is fixed inside the column by, for example, being installed on a plate inside the continuous multi-stage distillation column or being installed in the form of the packing. In the case of a catalyst that dissolves in the starting material or the reaction liquid, it is preferable to feed the catalyst into the distillation column from a position above the middle portion of the distillation column. In this case, the catalyst liquid dissolved in the starting material or reaction liquid may be introduced into the column together with the starting material, or may be introduced into the column from a different inlet from the starting material. The amount of the catalyst used in the present invention varies depending on the type thereof, the types and proportions of the starting material compounds, and reaction conditions such as the reaction temperature and the reaction pressure. The amount of the catalyst is generally in a range of from 0.0001 to 30% by weight, preferably 0.05 to 10% by weight, more preferably 0.001 to 1% by weight, based on the total weight of the starting material.

The reaction time for the transesterification reaction carried out in the present invention is considered to equate to the average residence time of the reaction liquid in the continuous multi-stage distillation column. The reaction time varies depending on the type of the internal inside the distillation column and the number of stages, the amount fed into the column of the starting material, the type and amount of the catalyst, the reaction conditions, and so on. The reaction time is generally in a range of from 0.01 to 10 hours, preferably 0.05 to 5 hours, more preferably 0.1 to 3 hours.

The reaction temperature varies depending on the type of the starting material compounds used, and the type and amount of the catalyst. The reaction temperature is generally in a range of from 100 to 350° C. It is preferable to increase the reaction temperature so as to increase the reaction rate. If the reaction temperature is too high, then side reactions become liable to occur, for example production of by-products such as Fries rearrangement products of the diaryl carbonate and an alkyl aryl ether, and ester compounds thereof increases, which is undesirable. For this reason, the reaction temperature is preferably in a range of from 130 to 280° C., more preferably 150 to 260° C., yet more preferably 180 to 240° C. Moreover, the reaction pressure varies depending on the type of the starting material compounds used and the composition of the starting material, the reaction temperature, and so on. The reaction pressure may be any of a reduced pressure, normal pressure, or an applied pressure. The pressure at the top of the column is generally in a range of from 0.1 to $2 \times 10^7$ Pa, preferably $10^3$ to $10^6$ Pa, more preferably $5 \times 10^3$ to $10^5$ Pa.

The material constituting the continuous multi-stage distillation column used in the present invention is generally a metallic material such as carbon steel or stainless steel. In terms of the quality of the diaryl carbonate produced, stainless steel is preferable.

Hereinbelow, the present invention will be described in more detail with reference to the following Examples, but the present invention is not limited to the following Examples.

EXAMPLES

A halogen content was measured by means of an ion chromatography method.

Example 1

Continuous Multi-Stage Distillation Column

A continuous multi-stage distillation column as shown in FIG. 1 having L=3100 cm, D=500 cm, L/D=6.2, n=30, $D/d_1$=3.85, and $D/d_2$=11.1 was used. In this example, as the internal, two sets of Mellapak (total theoretical number of stages 11) were installed in the upper portion, and the sieve tray having the cross-sectional area per hole of approximately 1.3 cm² and a number of holes of approximately 250/m² was used in the lower portion.

<Reactive Distillation>

A mixture containing 18% by weight of methyl phenyl carbonate that had been obtained by subjecting a mixture containing dimethyl carbonate and phenol in a weight ratio of dimethyl carbonate/phenol=1.3 to a transesterification reaction was used as a starting material. This starting material contained 26% by weight of dimethyl carbonate, 6% by weight of anisole, 48% by weight of phenol, and 1% by weight of diphenyl carbonate, and further contained approximately 100 ppm of Pb(OPh)₂ as a catalyst. The starting material substantially did not contain halogens (outside the detection limit for the ion chromatography, i.e. 1 ppb or less).

The starting material was introduced into the continuous multi-stage distillation column at a flow rate of 66 ton/hr from a starting material inlet installed between the Mellapak and the sieve tray. Reactive distillation was carried out continuously under conditions of a temperature at the bottom of the column being 210° C., a pressure at the top of the column being $3 \times 10^4$ Pa, and a reflux ratio being 0.3. It was possible to attain stable steady state operation after 24 hours. The liquid continuously withdrawn from the bottom of the column contained 38.4% by weight of methyl phenyl carbonate and 55.6% by weight of diphenyl carbonate. It was found that the amount of diphenyl carbonate produced from the methyl phenyl carbonate per hour was 5.13 tons. The selectivity for the diphenyl carbonate based on the methyl phenyl carbonate reacted was 99%.

Prolonged continuous operation was carried out under these conditions. The amounts of diphenyl carbonate produced per hour at 500 hours, 2000 hours, 4000 hours, 5000 hours, and 6000 hours after attaining stable steady state (excluding the diphenyl carbonate contained in the starting material) were 5.13 tons, 5.13 tons, 5.14 tons, 5.14 tons, and 5.13 tons respectively, and the selectivities were 99%, 99%, 99%, 99%, and 99% respectively, and hence the operation was very stable. Moreover, the aromatic carbonates produced substantially did not contain halogens (1 ppb or less).

Example 2

Reactive distillation was carried out under the following conditions using the same continuous multi-stage distillation column as in Example 1.

<Reactive Distillation>

A mixture containing 21% by weight of methyl phenyl carbonate that had been obtained by subjecting a mixture containing dimethyl carbonate and phenol in a weight ratio of dimethyl carbonate/phenol=1.9 to a transesterification reaction was used as a starting material. This starting material contained 32% by weight of dimethyl carbonate, 5% by weight of anisole, 41% by weight of phenol, and 1% by weight of diphenyl carbonate, and further contained approximately 250 ppm of Pb(OPh)₂ as a catalyst. The starting material substantially did not contain halogens (outside the detection limit for the ion chromatography, i.e. 1 ppb or less).

The starting material was introduced into the continuous multi-stage distillation column at a flow rate of 80 ton/hr from a starting material inlet installed between the Mellapak and the sieve tray. Reactive distillation was carried out continuously under conditions of a temperature at the bottom of the column being 205° C., a pressure at the top of the column being $2 \times 10^4$ Pa, and a reflux ratio being 0.5. It was possible to attain stable steady state operation after 24 hours. The liquid continuously withdrawn from the bottom of the column contained 36.2% by weight of methyl phenyl carbonate and 60.8% by weight of diphenyl carbonate. It was found that the amount of diphenyl carbonate produced from the methyl phenyl carbonate per hour was 8.06 tons. The selectivity for the diphenyl carbonate based on the methyl phenyl carbonate reacted was 99%.

Prolonged continuous operation was carried out under these conditions. The amounts of diphenyl carbonate produced per hour at 500 hours, 1000 hours, 1500 hours, 2000 hours, and 2500 hours after attaining stable steady state (excluding the diphenyl carbonate contained in the starting material) were 8.06 tons, 8.07 tons, 8.07 tons, 8.06 tons, and 8.07 tons respectively, and the selectivities were 99%, 99%, 99%, 99%, and 99% respectively, and hence the operation was very stable. Moreover, the aromatic carbonates produced substantially did not contain halogens (1 ppb or less).

Example 3

Reactive distillation was carried out under the following conditions using the same continuous multi-stage distillation column as in Example 1, except that the cross-sectional area per hole of the sieve tray was made to be approximately 1.8 cm².

<Reactive Distillation>

A mixture containing 16% by weight of methyl phenyl carbonate that had been obtained by subjecting a mixture containing dimethyl carbonate and phenol in a weight ratio of dimethyl carbonate/phenol=1.4 to a transesterification reaction was used as a starting material. This starting material contained 27% by weight of dimethyl carbonate, 7% by weight of anisole, 49% by weight of phenol, and 0.5% by weight of diphenyl carbonate, and further contained approximately 200 ppm of Pb(OPh)$_2$ as a catalyst. The starting material substantially did not contain halogens (outside the detection limit for the ion chromatography, i.e. 1 ppb or less).

The starting material was introduced into the continuous multi-stage distillation column at a flow rate of 94 ton/hr from a starting material inlet installed between the Mellapak and the sieve tray. Reactive distillation was carried out continuously under conditions of a temperature at the bottom of the column being 215° C., a pressure at the top of the column being 2.5×10$^4$ Pa, and a reflux ratio being 0.4. It was possible to attain stable steady state operation after 24 hours. The liquid continuously withdrawn from the bottom of the column contained 35.5% by weight of methyl phenyl carbonate and 59.5% by weight of diphenyl carbonate. It was found that the amount of diphenyl carbonate produced from the methyl phenyl carbonate per hour was 7.28 tons. The selectivity for the diphenyl carbonate based on the methyl phenyl carbonate reacted was 99%.

Prolonged continuous operation was carried out under these conditions. The amounts of diphenyl carbonate produced per hour at 500 hours, 1000 hours, 1500 hours, 2000 hours, and 2500 hours after attaining stable steady state (excluding the diphenyl carbonate contained in the starting material) were 7.28 tons, 7.28 tons, 7.29 tons, 7.29 tons, and 7.28 tons respectively, and the selectivities were 99%, 99%, 99%, 99%, and 99% respectively, and hence the operation was very stable. Moreover, the aromatic carbonates produced substantially did not contain halogens (1 ppb or less).

INDUSTRIAL APPLICABILITY

When continuously producing aromatic carbonates containing a diaryl carbonate as a main product by taking an alkyl aryl carbonate as a starting material, which is obtainable through a transesterification reaction between a dialkyl carbonate and an aromatic monohydroxy compound, using a continuous multi-stage distillation column in which a catalyst is present, and continuously feeding the starting material into the continuous multi-stage distillation column, the present invention is suitable as a specific process that enables the diaryl carbonate to be produced with high selectivity and high productivity stably for a prolonged period of time on an industrial scale of not less than 1 ton per hour.

The invention claimed is:

1. A process for the production of an aromatic carbonate containing a diaryl carbonate as a main product from a strating material comprising an alkyl aryl carbonate, which is obtainable through a transesterification reaction between a dialkyl carbonate and an aromatic monohydroxy compound, which comprises the steps of:
   (i) continuously feeding said starting material into a continuous multi-stage distillation column in which a catalyst is present;
   (ii) carrying out the reaction in the column to produce a dialkyl carbonate and the diaryl carbonate;
   (iii) continuously withdrawing a low boiling point reaction mixture containing said produced the dialkyl carbonate from an upper portion of the column in a gaseous form and continuously withdrawing a high boiling point reaction mixture containing the diaryl carbonate from a lower portion of the column in a liquid form, wherein said continuous multi-stage distillation column comprises a structure having a pair of end plates above and below a cylindrical trunk portion having a length L (cm) and an inside diameter D (cm), and having an internal with a number of stages n thereinside, and comprises a gas outlet having an inside diameter $d_1$ (cm) at the top of the column or in an upper portion of the column near to the top, a liquid outlet having an inside diameter $d_2$ (cm) at the bottom of the column or in a lower portion of the column near to the bottom, at least one inlet provided in the upper portion and/or a middle portion of the column below the gas outlet, and at least one inlet provided in the lower portion of the column above the liquid outlet, wherein
   (1) said length L (cm) satisfies the following formula (1), $$1500 \leq L \leq 8000 \tag{1},$$

(2) said inside diameter D (cm) of the column satisfies the following formula (2), $$100 \leq D \leq 2000 \tag{2},$$

(3) a ratio of said length L (cm) to said inside diameter D (cm) of the column satisfies the following formula (3), $$2 \leq L/D \leq 40 \tag{3},$$

(4) said number of stages n satisfies the following formula (4), $$10 \leq n \leq 80 \tag{4},$$

(5) a ratio of said inside diameter D (cm) of the column to said inside diameter $d_1$ (cm) of the gas outlet satisfies the following formula (5), $$2 \leq D/d_1 \leq 15 \tag{5, and}$$

(6) a ratio of said inside diameter D (cm) of the column to said inside diameter $d_2$ (cm) of the liquid outlet satisfies the following formula (6), $$5 \leq D/d_2 \leq 30 \tag{6}.$$

2. The process according to claim 1, wherein distillation is carried out simultaneously in said step (ii).

3. The process according to claim 1, wherein said aromatic carbonate containing the diaryl carbonate as the main product is continuously produced and an amount of said diaryl carbonate produced is not less than 1 ton per hour.

4. In a process for the production of an aromatic carbonate containing a diaryl carbonate as a main product in which the aromatic carbonate containing the diaryl carbonate as the main product is produced continuously by continuously feeding an alkyl aryl carbonate as a starting material, which is obtainable through a transesterification reaction between a dialkyl carbonate and an aromatic monohydroxy compound, into a continuous multi-stage distillation column in which a catalyst is present, carrying out the reaction and the distillation simultaneously in the column, continuously withdrawing a low boiling point reaction mixture containing a produced dialkyl carbonate from an upper portion of the column in a gaseous form, and continuously withdrawing a high boiling point reaction mixture containing the diaryl carbonate from a lower portion of the column in a liquid form, the improvement in which said continuous multi-stage distillation column comprises a structure having a pair of end plates above and below a cylindrical trunk portion having a length L (cm) and an inside diameter D (cm), and having an internal with a number of stages n thereinside, and comprises a gas outlet having an inside diameter $d_1$ (cm) at the top of the column or in an upper portion of the column near to the top, a liquid outlet having an inside diameter $d_2$ (cm) at the bottom of the column or in a lower portion of the column near to the bottom, at least one inlet provided in the upper portion and/or a middle portion of the column below the gas outlet, and at least one inlet provided in the lower portion of the column above the liquid outlet, wherein (1) said length L (cm) satisfies the following formula (1), $$1500 \leq L \leq 8000 \tag{1},$$

(2) said inside diameter D (cm) of the column satisfies the following formula (2), $$100 \leq D \leq 2000 \tag{2},$$

(3) a ratio of said length L (cm) to said inside diameter D (cm) of the column satisfies the following formula (3), $$2 \leq L/D \leq 40 \tag{3},$$

(4) said number of stages n satisfies the following formula (4), $$10 \leq n \leq 80 \tag{4},$$

(5) a ratio of said inside diameter D (cm) of the column to said inside diameter $d_1$ (cm) of the gas outlet satisfies the following formula (5), $$2 \leq D/d_1 \leq 15 \tag{5, and}$$

(6) a ratio of said inside diameter D (cm) of the column to said inside diameter $d_2$ (cm) of the liquid outlet satisfies the following formula (6), $$5 \leq D/d_2 \leq 30 \tag{6}.$$

5. The process according to claim 4, wherein an amount of the diaryl carbonate produced is not less than 1 ton per hour.

6. The process according to claim 1, wherein $d_1$ and $d_2$ satisfy the following formula (7)

$$1 \leq d_1/d_2 \leq 6 \tag{7}.$$

7. The process according to claim 1, wherein L, D, L/D, n, $D/d_1$, and $D/d_2$ for said continuous multi-stage distillation column satisfy the following formulae; $2000 \leq L \leq 6000$, $150 \leq D \leq 1000$, $3 \leq L/D \leq 30$, $15 \leq n \leq 60$, $2.5 \leq D/d_1 \leq 12$, and $7 \leq D/d_2 \leq 25$, respectively.

8. The process according to claim 1, wherein L, D, L/D, n, $D/d_1$, and $D/d_2$ for the continuous multi-stage distillation column satisfy the following formulae; $2500 \leq L \leq 5000$, $200 \leq D \leq 800$, $5 \leq L/D \leq 15$, $20 \leq n \leq 50$, $3 \leq D/d_1 \leq 10$, and $9 \leq D/d_2 \leq 20$, respectively.

9. The process according to claim 1, wherein said continuous multi-stage distillation column is a distillation column having a packing and a tray as the internal.

10. The process according to claim 9, wherein said continuous multi-stage distillation column is a distillation column having, as the internal, the packing in the upper portion of the column, and the tray in the lower portion of the column.

11. The process according to claim 9, wherein said packing of the internal is a structured packing.

12. The process according to claim 9, wherein said tray of the internal is a sieve tray having a sieve portion and a down comer portion.

13. The process according to claim 9, wherein said packing of the internal is one or more of the structured packing, and said trays is a sieve tray having a sieve portion and a down comer portion.

14. The process according to claim 11, wherein said structured packing is at least one selected from the group consisting of Mellapak, Gempak, TECHNO-PAK, FLEXI-PAK, a Sulzer packing, a Goodroll packing and a Glitchgrid.

15. The process according to claim 12, wherein said sieve tray has 100 to 1000 holes/m² in the sieve portion.

16. The process according to claim 12, wherein the cross-sectional area per hole of said sieve tray is in a range of from 0.5 to 5 cm².

17. The process according to claim 13, wherein said structured packing is at least one selected from the group consisting of Mellapak, Gempak, TECHNO-PAK, FLEXI-PAK, a Sulzer packing, a Goodroll packing and a Glitchgrid, aid sieve tray has 100 to 1000 holes/m² in the sieve portion, and the cross-sectional area per hole of said sieve tray is in a range of from 0.5 to 5 cm².

* * * * *